United States Patent
Hilbold et al.

(10) Patent No.: US 12,280,189 B2
(45) Date of Patent: Apr. 22, 2025

(54) DIALYSIS SYSTEM HAVING FIXED WATER PREPARATION UNITS

(71) Applicant: B. Braun Avitum AG, Melsungen (DE)

(72) Inventors: Freddy Hilbold, Loerrach-Brombach (DE); Stephan Krietemeyer, Kandern (DE); Philipp Odernheimer, Kassel (DE)

(73) Assignee: B. Braun Avitum AG, Melsungen (DE)

( * ) Notice: Subject to any disclaimer, the term of this patent is extended or adjusted under 35 U.S.C. 154(b) by 672 days.

(21) Appl. No.: 17/630,327

(22) PCT Filed: Jul. 28, 2020

(86) PCT No.: PCT/EP2020/071264
§ 371 (c)(1),
(2) Date: Jan. 26, 2022

(87) PCT Pub. No.: WO2021/023579
PCT Pub. Date: Feb. 11, 2021

(65) Prior Publication Data
US 2022/0249752 A1    Aug. 11, 2022

(30) Foreign Application Priority Data
Aug. 2, 2019    (DE) .................... 10 2019 121 003.8

(51) Int. Cl.
*A61M 1/16*    (2006.01)
*A61M 1/14*    (2006.01)

(52) U.S. Cl.
CPC .......... *A61M 1/1656* (2013.01); *A61M 1/152* (2022.05); *A61M 2205/6045* (2013.01)

(58) Field of Classification Search
None
See application file for complete search history.

(56) References Cited

U.S. PATENT DOCUMENTS

| 4,808,287 A | 2/1989 | Hark |
| 9,259,522 B2 | 2/2016 | Wehmeyer et al. |

(Continued)

FOREIGN PATENT DOCUMENTS

| CN | 104288850 A | 1/2015 |
| DE | 4331102 A1 | 3/1995 |

(Continued)

OTHER PUBLICATIONS

Notice of Allowance received in Japanese Application No. 2022-506546 dated Jun. 11, 2024, with translation, 2 pages.

(Continued)

*Primary Examiner* — Peter Keyworth
(74) *Attorney, Agent, or Firm* — Christopher A. Rothe; CM Law

(57) ABSTRACT

A stationary dialysis system includes at least two separate water preparation units, preferably of the osmosis type, which can be fluidically connected and/or separated to/from at least two separate ring lines according to selectable supply variants. A plurality of fixed, unchangeable hydraulic circuits representing the supply variants can be introduced into a circuit receiving means of the dialysis system for fluidically connecting and/or separating of the water preparation units to/from the ring lines.

11 Claims, 7 Drawing Sheets

(56) References Cited

U.S. PATENT DOCUMENTS

| | | |
|---|---|---|
| 9,827,362 B2 | 11/2017 | Alvensleben |
| 2014/0083917 A1 | 3/2014 | Okabe et al. |
| 2015/0021245 A1 | 1/2015 | Rohde et al. |
| 2015/0021248 A1* | 1/2015 | Alvensleben ....... A61M 1/1664 210/181 |

FOREIGN PATENT DOCUMENTS

| | | |
|---|---|---|
| DE | 10256584 A1 | 5/2004 |
| DE | 102008013109 A1 | 9/2009 |
| DE | 102013107673 A1 | 1/2015 |
| EP | 1234590 A1 | 8/2002 |
| EP | 1614437 A1 | 1/2006 |
| JP | 2006314458 A | 11/2006 |
| WO | 03040042 A1 | 5/2003 |
| WO | 2012095301 A2 | 7/2012 |

OTHER PUBLICATIONS

Search Report received in German Application No. 10 2019 121 003.8 dated Jul. 14, 2020, with translation, 10 pages.
Search Report received in International Application No. PCT/EP2020/071264 dated Oct. 14, 2020, with translation, 5 pages.
Written Opinion received in International Application No. PCT/EP2020/071264 dated Oct. 14, 2020, with translation, 13 pages.
Office Action received in Chinese Application No. 202080052040.4 dated Sep. 29, 2023, with translation, 16 pages.

* cited by examiner

DIALYSIS SYSTEM HAVING FIXED WATER PREPARATION UNITS

CROSS-REFERENCES TO RELATED APPLICATIONS

This application is the United States national phase entry of International Application No. PCT/EP2020/071264, filed Jul. 28, 2020, and claims priority to German Application No. 10 2019 121 003.8, filed Aug. 2, 2019. The contents of International Application No. PCT/EP2020/071264 and German Application No. 10 2019 121 003.8 are incorporated by reference herein in their entireties.

FIELD

The present disclosure relates to a stationary dialysis system comprising at least two stationary water preparation units, preferably of the osmosis type, to the respective outlet of which a water supply line is connected, at least two ring line inlets which have a plurality of branch connections which can be selectively fluidically coupled to stationary and/or mobile dialysis units, at least two ring line returns/ring line return lines/drain lines, via which unused dialysis water can be returned from the dialysis units, and tubular connecting elements which, in an installed state, fluidically connect the ring lines on the inlet side to the water supply lines and the ring lines on the outlet side to the drain lines.

BACKGROUND

As the number of dialysis treatment units increases, two or more water preparation units and two or more ring lines connectable thereto are also increasingly being installed in stationary dialysis systems. The main idea here is that in the event of failure of one water preparation unit or in the event of arising maintenance work on one water preparation unit, the one or more remaining water preparation units shall supply the ring lines with dialysis permeate/dialysis fluid. However, this requires a hydraulic change in the feed into the ring lines or a hydraulic change in the connection between the water preparation units and the ring lines. During maintenance of a water preparation unit, it is for example necessary to fluidically separate this unit from the ring lines, and the remaining water preparation unit then supplies the ring lines with dialysis fluid.

Here, the ring lines to be supplied are located in most cases in spatially separate treatment units (rooms or floors). However, information about the operating state of the connected water preparation unit must be available in each treatment unit so that patients are not exposed to any risk from unrecognized or unperformed disinfection processes, i.e. contaminated ring lines, or operational malfunctions of the connected medical technology systems, such as the water preparation unit or the dialysis units. This information from the medical technology systems is usually transmitted to remote controls (remote control module), which can display the operating state of the connected medical technology systems. Missing information (e.g. about ongoing disinfection processes) or incorrectly transmitted information poses a considerable risk to patients here.

In conventional stationary dialysis systems and their ring line assemblies or ring line arrangements, manually switchable hydraulic valves, e.g. 3/2-way valves, are installed between the water preparation units and the ring lines. By switching these hydraulic valves, individual line sections can be bypassed via bypasses introduced into the fluidic connection between the water preparation units and the ring lines, thus changing the feed into the ring lines. However, from a mathematical point of view, more senseless switching variants than sensible switching variants are possible in this case. Only the switching variants or valve positions that are displayed to the operator on a depiction arranged next to such a ring line assembly ("ring line splitter") are permitted switching variants.

In general, recognized risks must in addition be prevented as best as possible in medical technology systems, preferably by design measures that make incorrect operation impossible (see ISO 14971). However, visual measures to indicate the risk, such as labeling, do not reduce the risk to the point of acceptance.

An example of a stationary dialysis system with only one stationary water preparation unit is disclosed in DE 10 2013 107 673 A1. Here, a water supply line for supplying treated water is connected to the outlet of the water preparation unit, which in turn has a number of branch connections to which dialysis machines are fluidically coupled in a selective manner. In addition, the dialysis system has a drain line for the disposal of used dialysis fluid.

EP 2 663 345 B1, on the other hand, discloses a dialysis system having a stationary production unit for producing dialysis fluid, a hose-shaped or tubular line member for conducting the dialysis fluid, and a plurality of dialysis treatment units. The dialysis treatment units are connected to the line member by means of connection members. The flow of dialysis fluid to the dialysis treatment units is controlled by switching a plurality of valves arranged in the line member.

However, conventional stationary dialysis systems having ring line arrangements that can be switched via hydraulic valves always have the disadvantage that, due to non-indicated disinfection processes in the supply lines after switching between them, there is an increased risk of poisoning the patients due to remaining disinfection liquid. Furthermore, due to incorrect positions of the 3/2-way valves, disinfection liquid (hot/chemical) can be mistakenly introduced into the connected ring lines. Furthermore, possible leakages of the valves designed as ball valves (initial fault) cannot be detected. In the line sections that are not flushed after switching, dead zones can occur in which dialysis fluid collects and therefore contaminations can easily develop.

SUMMARY

The object underlying the present disclosure is to improve or eliminate disadvantages of the prior art. In particular, it is intended to provide a stationary dialysis system having a plurality of stationary water preparation units, preferably of the osmosis type, for the treatment of water to carry out a dialysis operation, which excludes unintended operating states and thus prevents any possible endangerment of the patients due to possible leaks in the connection lines between the water preparation units and the dialysis units or incorrect connection of the dialysis units. In addition, safe switching of the feed of dialysis fluid into optionally one or more ring lines by one person shall be made possible and, at the same time, dead zones in the hydraulic system (e.g. in the area of ball valves) shall be avoided by design in order to prevent bacterial contamination in the water supply. The dialysis system according to the disclosure shall furthermore be capable of reliably transmitting and displaying operating and/or alarm signals when the supply type is switched.

The main concept of the disclosure is to show only useful switching variants/supply variants by means of different geometric/hydraulic designs of the fluidic connection between the water preparation units and the ring lines in a valveless manner. In other words, according to the disclosure, the hydraulic switching device which is known from the prior art and which, using manually or electrically adjustable valves, fluidically connects or separates two or more separate (stationary) water preparation units to/from two or more separate (stationary) ring lines in freely selectable, different combination variants/supply variants depending on the valve positions, shall be replaced by a number (plurality) of so-called coupling masks/connection masks (hydraulic circuits) with in each case fixed or unchangeable (since valveless) combination variant which is inserted in/into a (stationary) mask receptacle (circuit receiving means) (to which the water preparation units/systems and ring lines as well as, if applicable, also drain lines are permanently connected) and thus connects or separates the water preparation units to/from the ring lines and, if applicable, drain lines according to this one mask-specific combination variant. This means that a plurality of coupling masks or a set of coupling masks is provided, each mask representing one (or at most two) coupling variant(s), and the masks can be (alternately) inserted into the mask receptacle in a selected manner. In other words, for the fluidic connection and/or separation of the water preparation units to/from the ring lines, a hydraulic circuit composed of a plurality of fixed, unchangeable hydraulic circuits representing the supply variants is inserted into a circuit receiving means of the dialysis system, or a plurality of such hydraulic circuits can be inserted into the circuit receiving means for the fluidic connection and/or separation of the water preparation units to/from the ring lines. In this connection, it is preferred to insert or integrate into the mask receptacle at least one sensor which recognizes the mask currently inserted in each case on the basis of the fluid lines or connection lines arranged therein or a label and sends a signal corresponding to the respective combination variant realized by the current mask to the currently connected (mobile) dialysis units/machines.

According to the disclosure, the tubular connecting elements (fluid lines) can accordingly be arranged for this purpose on a mounting plate (mask) which can be installed in a housing, preferably a control cabinet (mask receptacle), with connection points for the water supply lines, the ring lines and the drain lines, which connection points are designed as clamp-like connecting clips. In other words, the connecting elements are pre-assembled on the mounting plate, which is then inserted into the housing in the form of the above-mentioned mask together with the connecting elements.

In this connection, the connecting clips are preferably designed in the form of a hose clamp, which has an upper and lower shell connected by a hinge and a locking mechanism for locking the upper shell relative to the lower shell. The connecting elements, in turn, can have, preferably at their end sections, one connecting flange each, which can be inserted into the respective lower shell when the connecting elements are installed and can be secured by the locking mechanism after the upper shell has been folded down.

In addition, it is advantageous for the connection points to be designed with a, preferably constructional, coding and for the connecting elements to be designed with a, preferably constructional, coding corresponding to the coding of the connection points. Preferably, the coding of the connection points can be designed as recesses and the coding of the connecting elements as projections which, in the installed state of the connecting elements, engage in the recesses of the connection points so that incorrect installation of the mounting plate (connection mask) together with the connecting elements is made impossible by the constructional design. Undetected migration of disinfectant into the ring lines is thus ruled out.

Furthermore, it is advantageous for the dialysis system according to the disclosure to have sensors, preferably proximity sensors, for detecting the hydraulic circuit, in particular the installed state of the connecting elements or the connection mask, and a control unit which detects the sensor-detected hydraulic circuit or installed state and thus the supply variant and, based on this, controls a display unit designed with at least one operating indicator lamp. Together with the constructional design of the connecting elements or the connection masks, the risk of poisoning a patient can be reduced to a minimum by a logical evaluation of the installation state in the control unit.

When the dialysis system according to the disclosure is installed, the water preparation units and the dialysis units can preferably be arranged in such a way that they are locally separated from one another. In this context, it can also be advantageous for the water preparation units and the dialysis units to be located in different rooms, in particular on different floors, of a clinic. This can ensure that only qualified personnel have access to the water preparation units.

According to a preferred embodiment, the dialysis system can further be equipped with a remote control unit/remote control arranged on the dialysis units for displaying the supply variant or the installed state. In this case, the remote control unit can be designed as a screen on each dialysis unit. Alternatively, however, it is also conceivable to realize the remote control unit as a central, in particular mobile, display unit, for example in the form of a mobile computer unit, such as a tablet PC. By means of the remote control unit it is thus possible to monitor the installation state and thus the respective supply variant of the dialysis system as well as any error messages at any time.

In a preferred exemplary embodiment, a first supply variant can be realized by the connection mask, in particular by the mounting plate. In addition, by exchanging the one mounting plate with another mounting plate, a second supply variant can be realized, preferably on the same mask receptacle. It is hereby conceivable that a third supply variant can be realized by geometrically changing the orientation of the further mounting plate. According to the disclosure, the connecting elements in the first supply variant can be designed as substantially axially extending pipelines and in the second or third supply variant can be designed as a bifurcated pipe section with one inlet and two outlets ("split supplier") so that liquid only flows through the pipelines required for the respective supply variant, i.e. in the water supply lines, the ring lines, the drain lines, and thus, due to the design, no dead zones facilitating contamination are created in the pipelines.

BRIEF DESCRIPTION OF THE DRAWINGS

The present disclosure is described below with reference to a preferred exemplary embodiment. However, this embodiment is only illustrative in nature and is not intended to limit the scope of protection of the present disclosure.

DETAILED DESCRIPTION

A preferred exemplary embodiment of the present disclosure is described below on the basis of the accompanying drawings.

Figure 1:
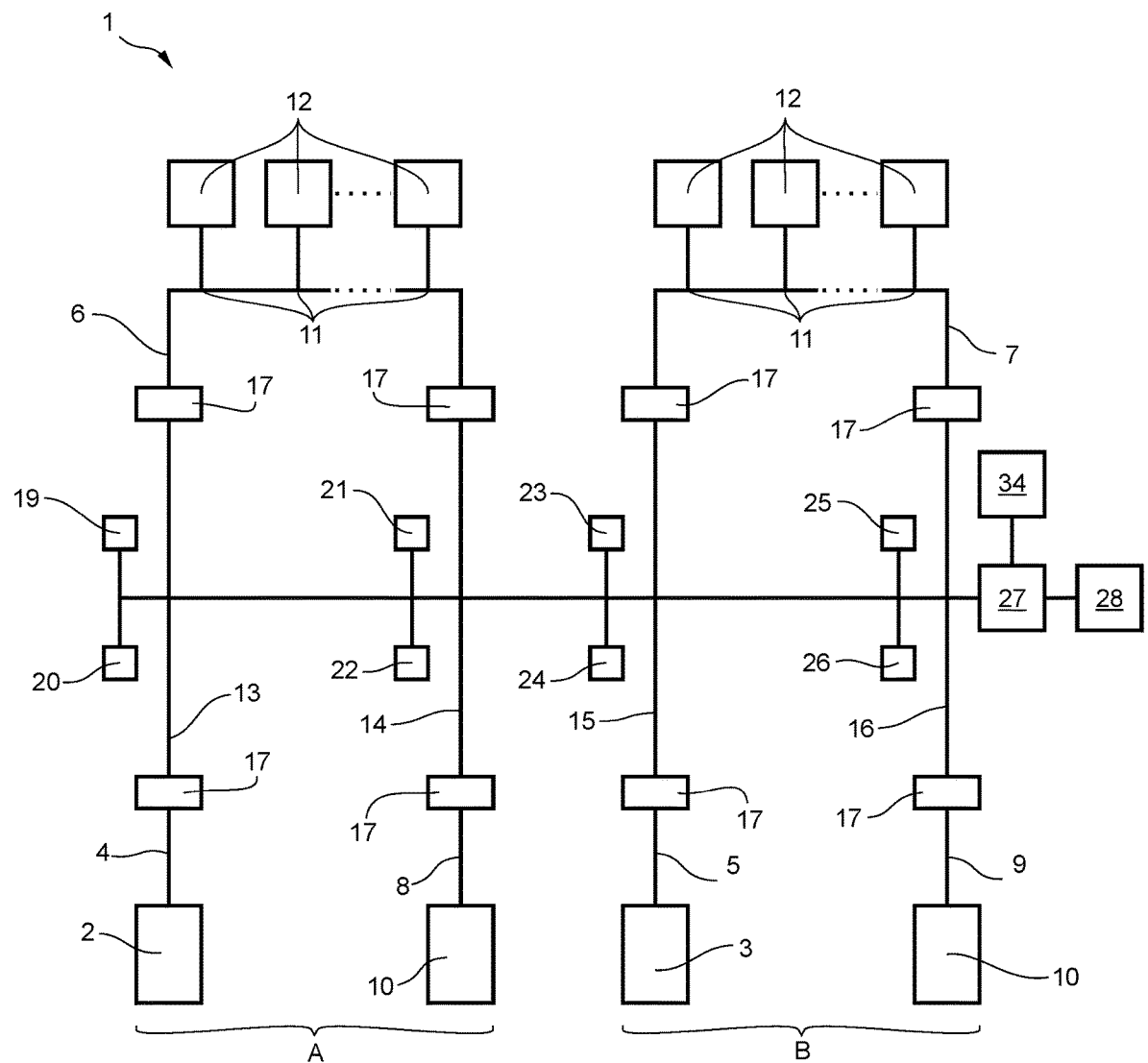
FIG. 1 is a schematic diagram of a first supply variant of a dialysis system according to a preferred exemplary embodiment of the present disclosure.

FIG. 1 shows a schematic diagram of a first switching arrangement/supply variant of a stationary dialysis system 1 according to a preferred exemplary embodiment of the present disclosure.

In the preferred exemplary embodiment, the dialysis system 1 has two reverse osmosis units 2, 3 for the treatment of water, to the respective outlet of which a water supply line 4, 5 is connected, via which the treated water is conducted to a mask receptacle designed as a main frame. Also connected to this mask receptacle are a first ring line 6, a second ring line 7 and two ring line return lines 8, 9 for returning unused dialysis permeate to a container 10 prior to water treatment, so that the treated water is distributed through a connection mask within the mask receptacle to the first ring line 6 and the second ring line 7 and, after flowing therethrough, can flow via the connection mask and the ring line return lines 8, 9 into the container 10. In this case, the reverse osmosis unit 2, the water supply line 4 and the ring line return line 8 form a first system A, and the reverse osmosis unit 3, the water supply line 5 and the ring line return line 9 form a second system B.

In the preferred exemplary embodiment, the reverse osmosis units 2, 3 are examples of a "water preparation unit" according to the disclosure. However, other water preparation units can of course also be used in addition to or instead of the reverse osmosis units 2, 3.

Along the first ring line 6 and the second ring line 7, a plurality of branch connections 11 is arranged in each case, to which, preferably mobile, dialysis units 12 can be connected. The dialysis units 12 are here locally decoupled from the reverse osmosis units 2, 3 and are located, for example in a clinic in which the dialysis system 1 is used, on a different floor than the reverse osmosis units 2, 3.

Figure 2:
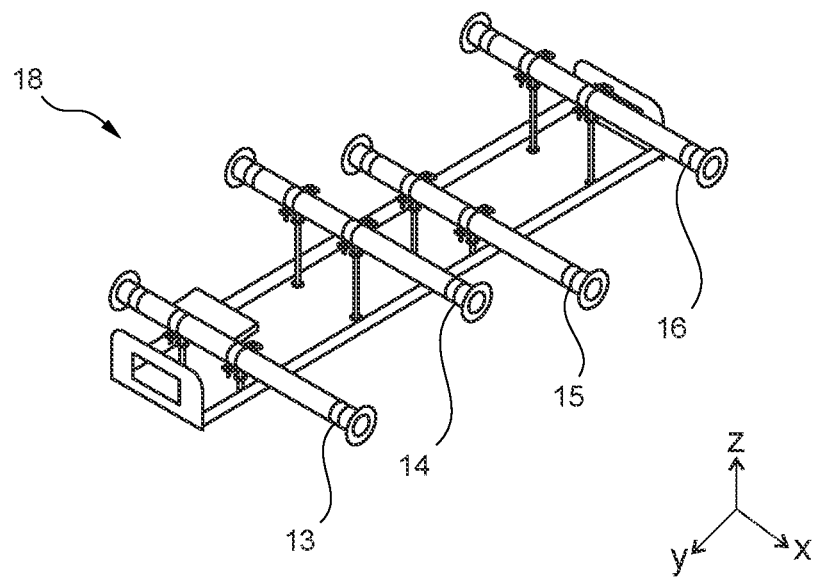
FIG. 2 is a view of a mounting plate with connecting elements according to the preferred exemplary embodiment.
Figure 3:
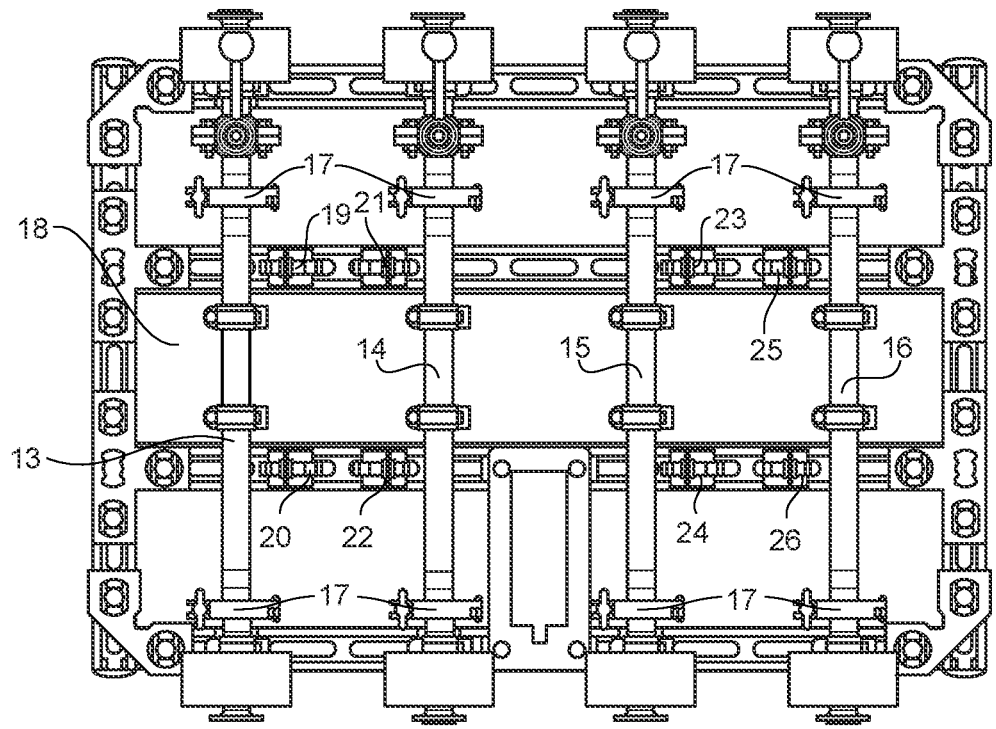
FIG. 3 is a view of the mounting plate with connecting elements according to the preferred exemplary embodiment in the installed state.

For the fluidic connection of the reverse osmosis units 2, 3 and the dialysis units 12 as well as the dialysis units 12 and the drain lines 8, 9, tubular connecting elements 13, 14, 15, 16 shown in FIG. 2 are installed in the mask receptacle, as shown in FIG. 3. For this purpose, connection clips ("clamp connectors") 17 described below are immovably arranged in the mask receptacle for connecting the connecting elements 13, 14, 15, 16 to the water supply lines 4, 5, an inlet and outlet of the first ring line 6 and the second ring line 7, and to the ring line return lines 8, 9.

In other words, the connection clips 17 thus form defined connection points for establishing a fluidic connection between the reverse osmosis units 2, 3 and the dialysis units 12 as well as the dialysis units 12 and the drain lines 8, 9 when the connecting elements 13, 14, 15, 16 are installed. In the dialysis system 1 according to the preferred exemplary embodiment, the connecting clips 17 are arranged in the control cabinet in such a way that the connecting clips 17 of the water supply line 4 and the ring line return line 8 are opposite the connecting clips 17 of the inlet or outlet of the first ring line 6, and the connecting clips 17 of the water supply line 5 and the ring line return line 9 are opposite the connecting clips 17 of the inlet or outlet of the second ring line 7.

In this regard, the connecting clips 17 are designed in the form of a hose clamp which has an upper and lower shell connected by a hinge and a locking mechanism for locking the upper shell relative to the lower shell. In turn, as shown in FIG. 2, each of the end sections of the connecting elements 13, 14, 15, 16 has a connecting flange which can be inserted into the respective lower shell during the installation of the connecting elements 13, 14, 15, 16 and secured by the locking mechanism when the upper shell has been folded down.

Furthermore, the connecting clips 17 also have recesses/notches in which projections formed on the connecting elements 13, 14, 15, 16 engage as soon as they are installed. In other words, the connecting clips 17 and the connecting elements 13, 14, 15, 16 are designed in a constructionally coded manner by means of the recesses and the projections.

As shown in FIG. 2, the connecting elements 13, 14, 15, 16 are furthermore immovably arranged on a mounting plate (connection mask) 18 which is mounted in the mask receptacle. This immovable arrangement on the mounting plate 18 as well as the above-mentioned constructional coding by means of the recesses and projections permits only one installation state and thus only one supply variant. In other words, due to the coding of the connecting clips 17, only one installation state of the mounting plate 18 is mechanically possible since otherwise the connecting clips 17 cannot be closed.

In order to be able to detect whether and which connecting elements 13, 14, 15, 16 have been installed, proximity sensors 19, 20, 21, 22, 23, 24, 25, 26 are additionally arranged in the control cabinet. Here, the proximity sensors 19, 20 are arranged in the area of the connecting element 13 so that the proximity sensor 19 can detect a ring line-side section of the connecting element 13 and the proximity sensor 20 can detect a water supply-side section of the connecting element 13. Accordingly, the proximity sensors 23, 24 are also arranged in the area of the connecting element 15 so as to be able to detect a ring line-side section of the connecting element 15 and a water supply-side section of the connecting element 15, respectively. The proximity sensors 21, 22 and 25, 26 are arranged in the area of the connecting element 14 and 16, respectively, to detect ring line side sections and ring line return line side sections of the connecting elements 14 and 16, respectively.

Figure 4:
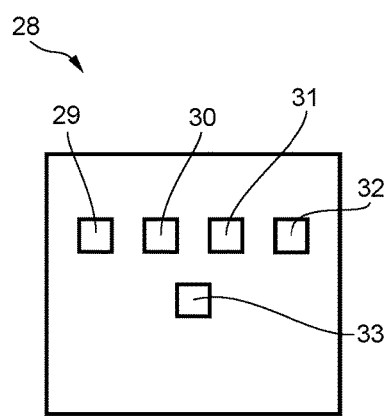
FIG. 4 is a schematic diagram of a display unit according to the present disclosure.

The proximity sensors 19, 20, 21, 22, 23, 24, 25, 26 output signals to a control unit 27 depending on the detection result, i.e. depending on the presence or absence of the corresponding section of the respective connecting element 13, 14, 15, 16. This control unit evaluates the detected installation state and controls a display unit 28 shown in FIG. 4. This display unit 28 is arranged outside the control cabinet, preferably on a door of the control cabinet, and in the preferred exemplary embodiment has five operating indicator lamps 29, 30, 31, 32, 33. The operating indicator lamps 29, 30, 31, 32, 33 can each be operated in two operating states (ON or "lights up"; OFF or "does not light up"). The operating indicator lamp 29 indicates whether the dialysis system 1 is switched on, i.e. is supplied with power. The operating indicator lamps 30, 31, 32 each indicate whether the first supply variant, a second supply variant or a third supply variant is present, and the operating indicator lamp 33 is used as an error indicator and is on as soon as the control unit 27 receives faulty signals.

In addition to controlling the operating indicator lamps 29, 30, 31, 32, 33, the control unit 27 additionally outputs information about the supply variant to a remote control unit ("remote control") 34 formed on the dialysis units 12. This remote control unit can be designed on each dialysis unit 12 in the form of a screen to which the information of the control unit 27 is output. Alternatively, the remote control unit 34 can also be a central unit which outputs the information of the control unit 27. For example, the remote control unit 34 can be a portable computer in the form of a tablet PC.

Figure 5:
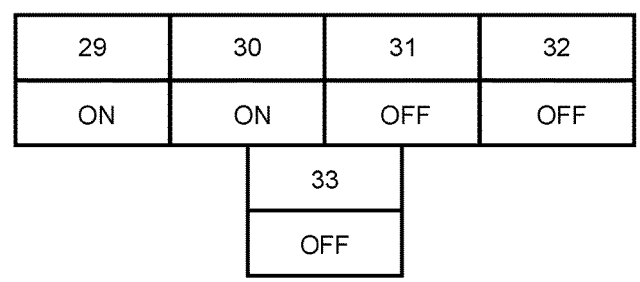
FIG. 5 is a tabular overview of a display state of operating indicator lamps of the display unit, which display state corresponds to the first supply variant.

In FIG. 5, the operating states of the operating indicator lamps 29, 30, 31, 32, 33 for the first supply variant are shown in tabular form. Here, the operating indicator lamps 29, 30 are on while the operating indicator lamps 31, 32, 33 are not on. This means that the dialysis system 1 is switched on and the first supply variant is selected.

In the first supply variant, as shown in FIG. 1 and FIG. 3, the reverse osmosis unit 2 and the water supply line 4 are fluidically connected to the inlet of the first ring line 6 via the connecting element 13. The connecting element 14 fluidically connects the outlet of the first ring line 6 to the ring line return line 8. The reverse osmosis unit 3 with the water supply line 5 is fluidically connected to the inlet of the second ring line 7 via the connecting element 15 whereas the connecting element 16 connects the outlet of the second ring line 7 to the ring line return line 9. This means that in the supply variant according to the first exemplary embodiment, the first ring line 6 is fed via the first system A while the second ring line 7 is supplied in a fluidically separate fashion via the second system B.

As is clear from FIG. 1, all proximity sensors 19, 20, 21, 22, 23, 24, 25, 26 detect the presence of the respective sections of the connecting elements 13, 14, 15, 16 and transmit these signals to the control unit 27.

In other words, in the first supply variant (direct supply; standard mode of operation), each of the two reverse osmosis units 2, 3 feeds independently into one of the two hydraulically separate ring lines 6, 7. System A feeds the first ring line 6 and system B feeds the second ring line 7. The first system A and the first ring line 6 are operated in a hydraulically separate manner from the second system B and the second ring line 7. The installation variant is detected via the proximity sensors 19, 20, 21, 22, 23, 24, 25, 26. The operating messages (dialysis operation, disinfection, alarm) of systems A, B are displayed at the connected remote control units 34.

Figure 6:
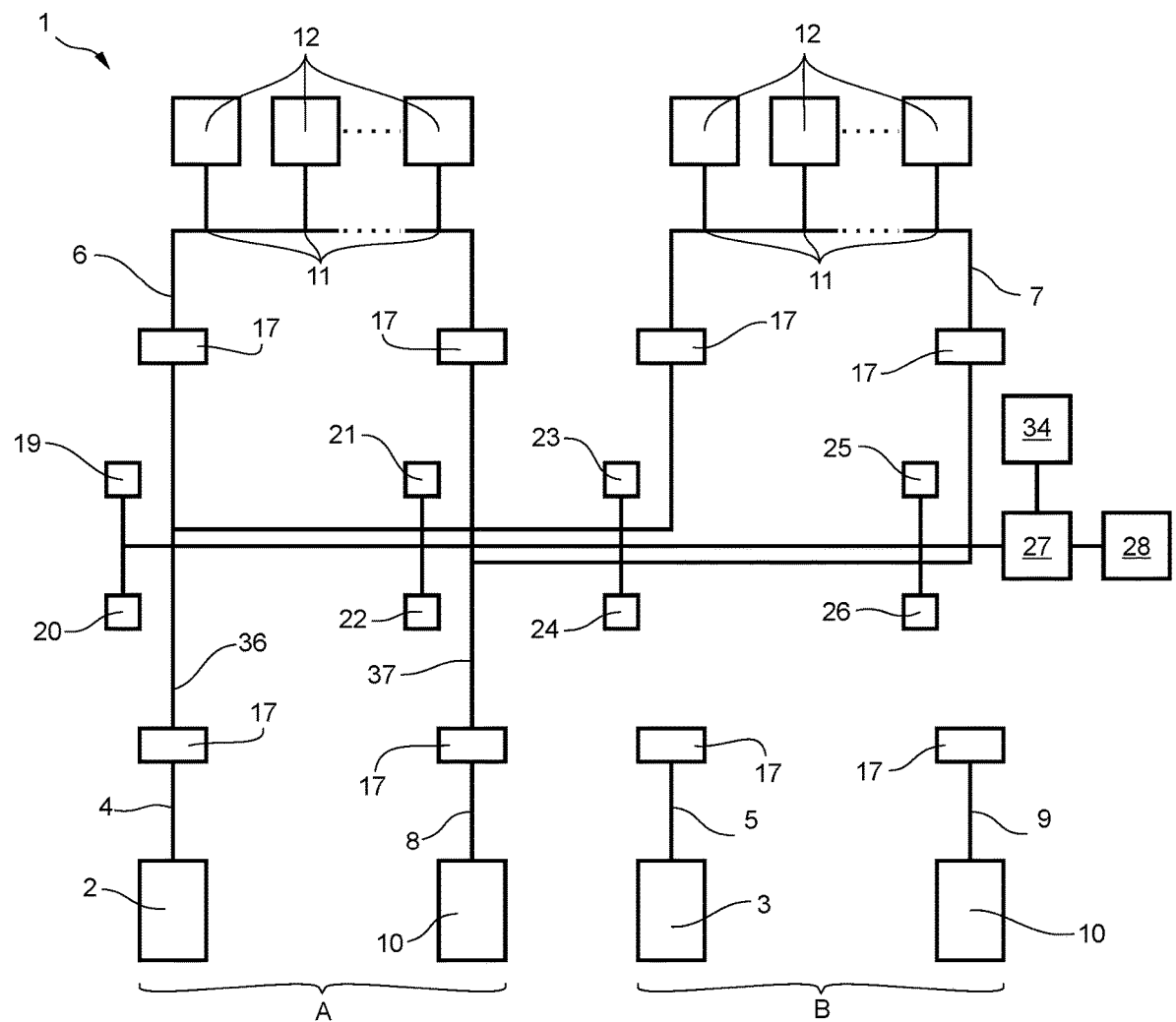
FIG. 6 is a schematic diagram of a second supply variant of the dialysis system according to the preferred exemplary embodiment of the present disclosure.

In FIG. 6, the dialysis system 1 according to the preferred exemplary embodiment is shown schematically in the second supply variant. In the following, the description of this second supply variant will only refer to the differences from the first supply variant shown in FIG. 1.

Figure 8:
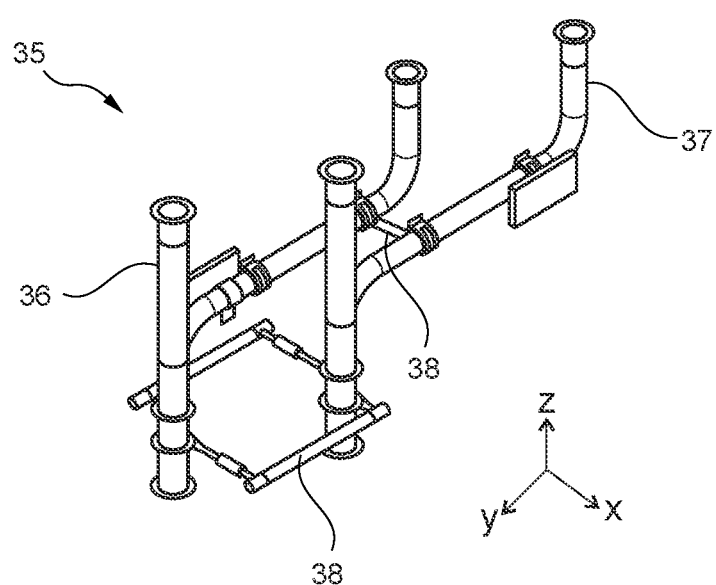
FIG. 8 is a view of a mounting plate with connecting elements according to the preferred exemplary embodiment for the second supply variant.

When the dialysis system 1 is operated in the second supply variant, the mounting plate 18 together with the connecting elements 13, 14, 15, 16 is replaced by a mounting plate 35 with connecting elements 36, 37 arranged immovably thereon. As shown in FIG. 8, the connecting elements 36, 37 are here designed as bifurcated pipe sections having one inlet and two outlets ("split supplier"). Due to fixed connections 38, for example via a clamp distance-rod combination, between the two connecting elements 36, 37, which can only be released with a special tool, it is not possible that only one of the connecting elements 36, 37 is installed, which would result in an impermissible supply variant.

In the second supply variant, the connecting element 36 connects the water supply line 4 to the inlet of the first ring line 6 and the inlet of the second ring line 7. The connecting element 37, on the other hand, connects the ring line return line 8 to the outlet of the first ring line 6 and the outlet of the second ring line 7. The unconnected connecting clips 17 of the second system B, i.e. the connecting clip 17 on the water supply line 5 and the ring line return line 9, are closed by dummy pieces.

Figure 7:
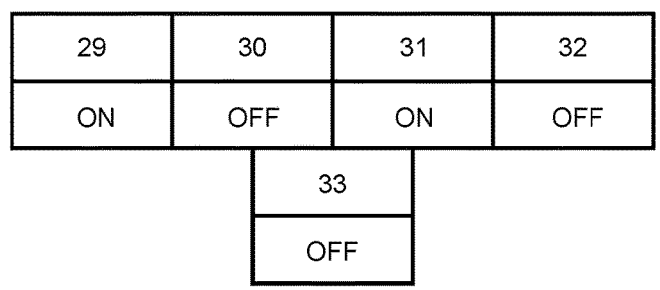
FIG. 7 is a tabular overview of the display state of the operating indicator lamps of the display unit, which display state corresponds to the second supply variant.

Consequently, in the second supply variant, the proximity sensors 19, 20, 21, 22, 23 and 25 detect an existing connecting element 36 and/or 37 whereas the two proximity sensors 24, 26 detect the absence of a connecting element. These detection results are sent by the proximity sensors 19, 20, 21, 22, 23, 24, 25, 26, analogously to the first supply variant, to the control unit 27, which based thereon in turn controls the display unit 28 together with the operating indicator lamps 29, 30, 31, 32, 33. The operating states of the operating indicator lamps 29, 30, 31, 32, 33 in the second supply variant are shown in tabular form in FIG. 7. Here, the operating indicator lamps 29, 31 light up while the operating indicator lamps 30, 32, 33 do not light up. This means that the dialysis system 1 is switched on and the second supply variant is selected.

In other words, by replacing the mounting plate 18 and inserting the mounting plate 35, the first system A is used to feed the dialysis permeate into the first ring line 6 and the second ring line 7. The open connection clips 17 of the second system B are closed by dummy pieces. The proximity sensors 19, 20, 21, 22, 23, 24, 25, 26 recognize the second supply variant as an admissible, permitted supply variant. The theoretically conceivable supply variant of a single ring line, i.e. the first ring line 6 or the second ring line 7, by the first system A and the second system B (corresponds in FIG. 8 to a rotation of the mounting plate 35 by 180° about the x-axis) is mechanically prevented by the constructional coding of the connecting clips 17 via recesses and projections. As mentioned above, an individual use of the two connecting elements 36, 37 is also excluded by the fixed connection 38 between the connecting elements 36, 37.

Figure 9:
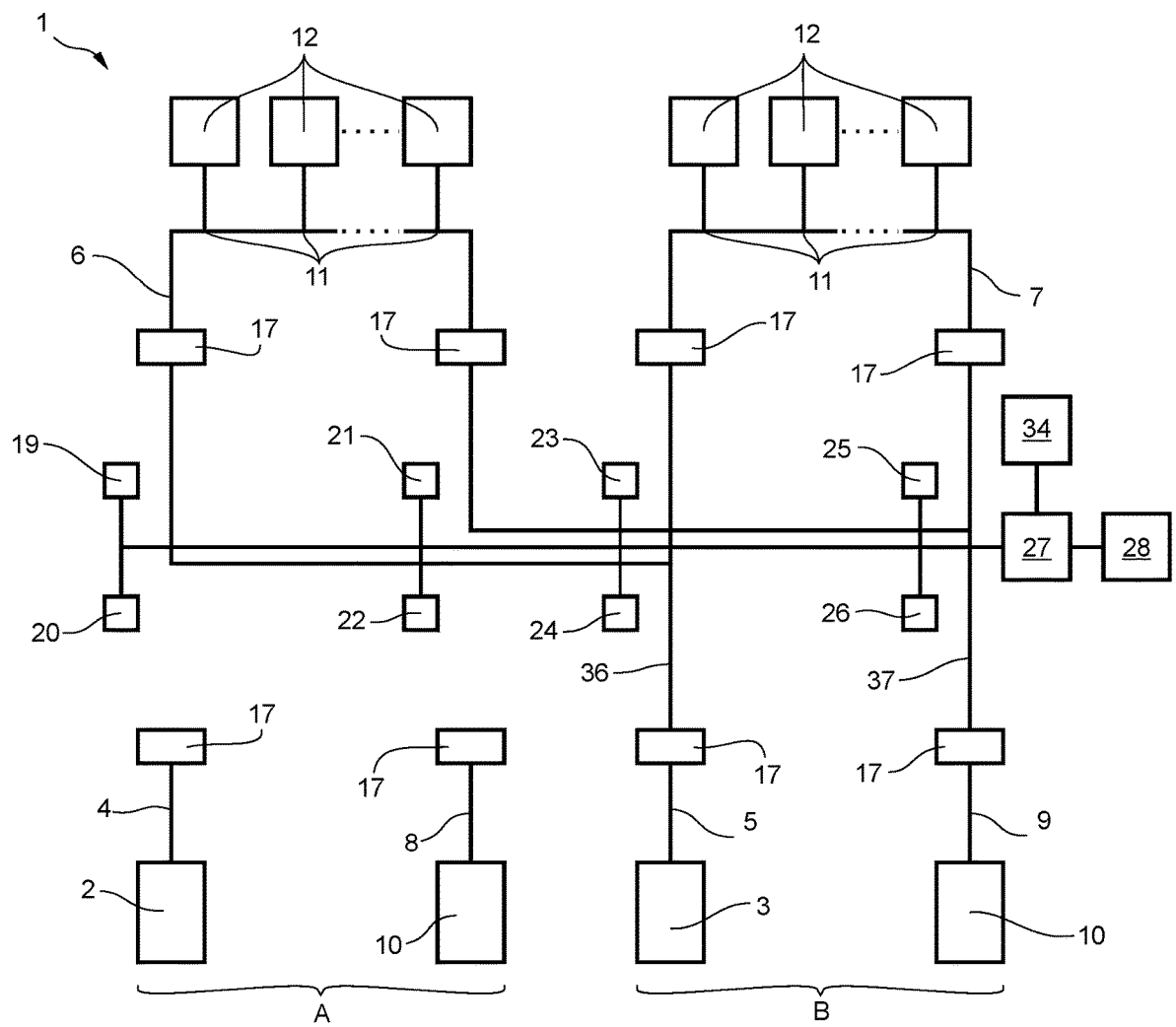
FIG. 9 is a schematic diagram of a third supply variant of the dialysis system according to the preferred exemplary embodiment of the present disclosure.

In FIG. 9, the dialysis system 1 according to the preferred exemplary embodiment is schematically shown in the third supply variant. In the following, the description of this third supply variant will only refer to the differences from the second supply variant shown in FIG. 6.

Figure 10:
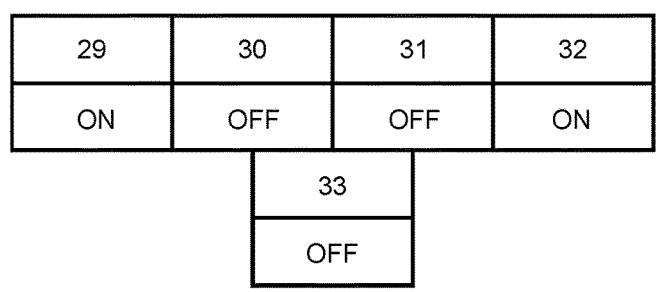
FIG. 10 is a tabular overview of the display state of the operating indicator lamps of the display unit, which display state corresponds to the third supply variant.
Figure 11:
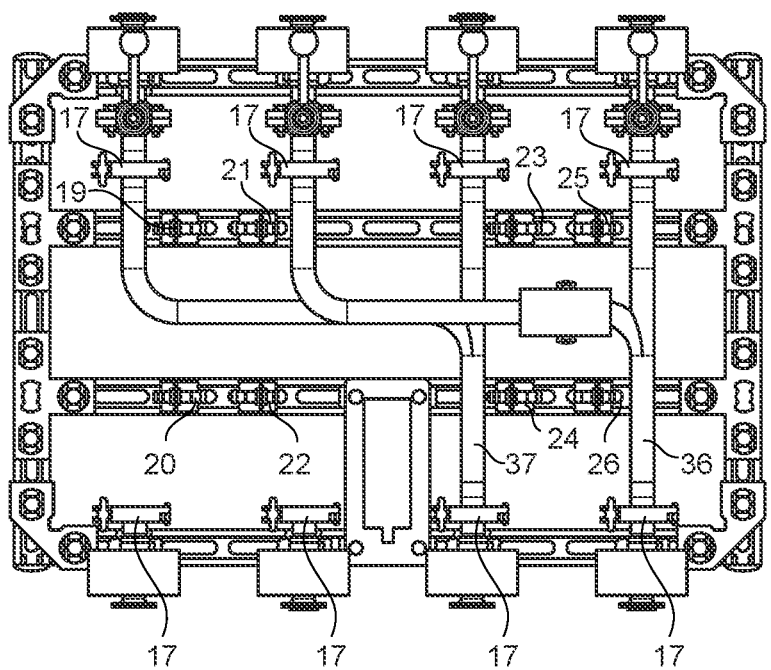
FIG. 11 is a view of the mounting plate with connecting elements according to the preferred exemplary embodiment in the installed state for the third supply variant.

When the dialysis system 1 is operated in the third supply variant, the mounting plate (connection mask) 35 with connecting elements 36, 37 immovably arranged thereon is turned by 180° along its vertical axis (corresponds to the z-axis in FIG. 8) compared to the second supply variant and then inserted as shown in FIG. 10.

Thus, in the third supply variant, the connecting element 36 connects the water supply line 5 to the inlet of the first ring line 6 and the inlet of the second ring line 7. The connecting element 37, on the other hand, connects the ring line return line 9 to the outlet of the first ring line 6 and the outlet of the second ring line 7. The unconnected connecting clips 17 of the second system A, i.e. the connecting clip 17 on the water supply line 4 and the ring line return line 8, are closed by dummy pieces.

Thus, in the second supply situation, the proximity sensors 19, 21, 23, 24, 25 and 26 detect an existing connecting element 36 and/or 37 whereas the two proximity sensors 20, 22 detect the absence of a connecting element. These detection results are sent by the proximity sensors 19, 20, 21, 22, 23, 24, 25, 26, analogously to the first or second supply variant, to the control unit 27, which based thereon in turn controls the display unit 28 together with the operating indicator lamps 29, 30, 31, 32, 33. The operating states of the operating indicator lamps 29, 30, 31, 32, 33 in the second supply variant are shown in tabular form in FIG. 9. Here, the operating indicator lamps 29, 32 light up while the operating indicator lamps 30, 31, 32 do not light up. This means that the dialysis system 1 is switched on and the third supply variant is selected.

In other words, by turning the mounting plate 35, the second system B can be used to feed the dialysis permeate into the first ring line 6 and the second ring line 7. The open connecting clips 17 of the first system A are closed by dummy pieces.

Impermissible supply variants, e.g. individual use of a connecting element 36, 37, are prevented by the constructional coding of the connecting clips 17 and the fixed connection 38 between the connecting elements 36, 37, and are indicated by the fact that the operating indicator lamp 33 lights up. In this case, the reverse osmosis units 2, 3 of the dialysis system 1 are switched to a fault mode.

The invention claimed is:

1. A stationary dialysis system comprising:
at least two water preparation units that are separate and configured to be fluidically connected and/or separated to/from at least two separate ring lines according to selectable supply variants,
wherein
a hydraulic circuit of a plurality of fixed, unchangeable hydraulic circuits representing the supply variants is inserted in a circuit receiving means of the dialysis system for fluidically connecting and/or separating of the at least two water preparation units to/from the at least two separate ring lines.

2. The dialysis system according to claim 1, further comprising at least two separate ring line return lines, which can be connected to the at least two separate ring lines via the plurality of fixed, unchangeable hydraulic circuits representing the supply variants.

3. The dialysis system according to claim 1, wherein the plurality of fixed, unchangeable hydraulic circuits representing the supply variants are designed as connecting elements that are tubular and arranged fixedly on a mounting plate.

4. The dialysis system according to claim 3, wherein the mounting plate together with the connecting elements is inserted in a main frame formed as the circuit receiving means with connection points designed as connection clips for the at least two separate ring lines, and for water supply lines connected to the at least two water preparation units.

5. The dialysis system according to claim 4, wherein the connection points are designed with a first coding and the connecting elements are designed with a second coding corresponding to the first coding.

6. The dialysis system according to claim 5, wherein the first coding is designed as recesses and the second coding is designed as projections which, in an installed state of the connecting elements, engage in the recesses of the connection points.

7. The dialysis system according to claim 1, further comprising sensors configured to detect said hydraulic circuit of said plurality of fixed, unchangeable hydraulic circuits and a supply variant.

8. The dialysis system according to claim 7, further comprising a control unit which detects an installed state detected by the sensors and, based thereon, controls a display unit equipped with at least one operating indicator light.

9. The dialysis system according to claim 1, further comprising dialysis units connected to the at least two separate ring lines, wherein the at least two water preparation units and dialysis units are locally separated from one another.

10. The dialysis system according to claim 9, further comprising a remote control unit which is central or arranged on the dialysis units for displaying a supply variant.

11. The dialysis system according to claim 1, further comprising at least two separate ring line return lines, which can be connected to the at least two separate ring lines via the plurality of fixed, unchangeable hydraulic circuits representing the supply variants,
wherein the plurality of fixed, unchangeable hydraulic circuits representing the supply variants are designed as connecting elements that are tubular and arranged fixedly on a mounting plate, and
wherein the mounting plate together with the connecting elements is inserted in a main frame formed as the circuit receiving means with connection points designed as connection clips for the at least two separate ring lines, the at least two separate ring line return lines, and for water supply lines connected to the at least two water preparation units.

\* \* \* \* \*